(12) United States Patent
Gunn et al.

(10) Patent No.: US 7,175,808 B2
(45) Date of Patent: Feb. 13, 2007

(54) MICRO-ORGANISM INACTIVATION SYSTEM

(75) Inventors: Andrew Gunn, Angus (GB); Ian David Cameron, Dundee (GB); Duncan Stephen Pepper, Edinburgh (GB)

(73) Assignee: Iatros Limited, Edinburgh (GB)

( * ) Notice: Subject to any disclaimer, the term of this patent is extended or adjusted under 35 U.S.C. 154(b) by 665 days.

(21) Appl. No.: 10/240,504

(22) PCT Filed: Mar. 30, 2001

(86) PCT No.: PCT/GB01/01426
§ 371 (c)(1),
(2), (4) Date: Sep. 30, 2002

(87) PCT Pub. No.: WO01/74407
PCT Pub. Date: Oct. 11, 2001

(65) Prior Publication Data
US 2003/0138346 A1  Jul. 24, 2003

(30) Foreign Application Priority Data
Mar. 31, 2000 (GB) ................................ 0007681.0

(51) Int. Cl.
*A61M 1/36* (2006.01)
(52) U.S. Cl. ..................... 422/44; 422/186.3; 210/748; 250/435
(58) Field of Classification Search ............. 422/24, 422/44, 186.3; 250/435, 437, 432 R, 455.11; 210/748
See application file for complete search history.

(56) References Cited
U.S. PATENT DOCUMENTS

| | | | |
|---|---|---|---|
| 2,309,124 A | | 1/1943 | Knott |
| 3,791,790 A | * | 2/1974 | Wyndham et al. .......... 210/251 |
| 3,814,680 A | * | 6/1974 | Wood ......................... 250/437 |
| 3,864,081 A | * | 2/1975 | Logrippo .................... 250/435 |
| 5,227,637 A | | 7/1993 | Herold et al. |
| 5,770,147 A | | 6/1998 | Muller |
| 6,099,735 A | * | 8/2000 | Kelada ........................ 210/652 |
| 6,586,172 B1 | * | 7/2003 | Gunn et al. .................... 435/2 |

FOREIGN PATENT DOCUMENTS

| | | |
|---|---|---|
| DE | 196 50 118 A1 | 6/1998 |
| WO | WO 97 46271 A1 | 12/1997 |
| WO | WO 00 20045 A1 | 4/2000 |

OTHER PUBLICATIONS

Pathlnaer MB Plasma. Baxter Biotech Group.

* cited by examiner

*Primary Examiner*—Krisanne Jastrzab
*Assistant Examiner*—Sean Conley
(74) *Attorney, Agent, or Firm*—Alston & Bird LLP

(57) ABSTRACT

A portable micro-organism inactivation system comprising: a casing mounting, a UV radiation source, a pump, and releasable tube support for supporting an elongate tube to define a flow path extending therethrough which is substantially free of substantial discontinuities are provided by the present invention. The elongate tube has a first portion and a second portion wherein the first portion has a UV-transparent wall. The first portion extends in close proximity to the UV radiation source within an irradiation zone thereof while the second portion is interfaced with the pump for pumping of fluid through the system so that substantially the whole of said individual fluid unit is exposed to a similar micro-organism inactivating level of UV-irradiation, while minimizing damage to the desired components thereof. The invention also provides a method of micro-organism inactivation in a fluid using a system of the invention.

18 Claims, 3 Drawing Sheets

MICRO-ORGANISM INACTIVATION SYSTEM

The present invention relates to a method of and apparatus for the inactivation of microorganisms in blood and blood products using light radiation and continuous flow and able to operate on individual plasma donations or small volume blood products.

Removal or inactivation of microorganisms (especially viruses and bacteria) from blood and blood products is increasingly required to ensure the highest standards of safety and product quality. The lability of many blood components, cells and proteins severely limits, however, the more stringent treatments normally applied to sterilize fluids. Various treatments have been used in blood and blood products processing laboratories such as filtration, heat, and X- and gamma ray radiation, organic solvents and detergents. Heat and radiation treatments however, usually require stabilizer to be added and later removed. Solvent and detergent processing also require removal of these materials. It is generally desirable to avoid adding or removing substances to blood or blood products. Existing procedures currently in place for treating blood products moreover only inactivate a proportion of virus types, for instance some viruses are extremely heat resistant and others are devoid of membranes and thus resist solvent-detergent treatment. Such viruses could be removed by filtration if they were large enough, but unfortunately the heat-stable and non-enveloped viruses such as parvovirus and hepatitis are too small to be effectively removed by filtration. An additional problem is that unknown viruses will also exist, and an ideal inactivation method should inactivate these as well. Currently regulatory authorities require a combination of two different inactivation techniques to be applied, which should be orthogonal or based on independent physico chemical principles.

In principle, light (especially ultraviolet light) would be an excellent choice as it adds nothing, is orthogonal to existing methods (such as heat, solvent-detergent, filtration and γ-radiation) and has been successfully used for some time in both air, surface and water sterilization. Unfortunately the use thereof when applied to fluids such as blood and blood products has been frustrated by the high degree of light adsorption thereof. Many blood products strongly adsorb light and ultra-violet light even more so, due to the presence of haemoglobin and plasma proteins in high concentration. The primary result of this is that light penetrates only a very short distance into the fluid and the bulk of it is shielded from any germicidal action. In the case of ultra-violet light, for example UV-C or 254 nm wavelength light as emitted by the common low pressure mercury discharge lamp, the depth of penetration (defined as the point where the light intensity has been reduced to one tenth of its initial value) into blood products such as albumin and immunoglobulin solutions will vary depending on the protein concentration from about 1.0 mm down to as little as 0.05 mm. Thus the majority of UV light applications to blood products have tried to solve this problem by working with thin films of solution much less than 1 mm thick. Limited success has been reported, either because the process is insufficiently effective, and viruses survive to transmit diseases, and/or because the labile blood factors are inactivated and the product is not useful. More recently, efforts have been made to identify chemical additives which can be used to synergise the effect of light (by enhancing its microbial killing power) and/or other additives have been identified which reduce the damage caused to labile blood factors without also reducing the microbial killing effect. A problem is that many of these additives are toxic, and need to be removed after treatment. Unfortunately no reliable methods exist to treat plasma so as to inactivate all known viruses, let alone unknown viruses, whilst leaving the labile factors intact and functional. Due to the particularly stringent safety requirements applicable to blood and blood products, and the relatively cumbersome and complex nature of the sterilization procedures currently in use, as far as we are aware, there has been no serious consideration by anyone else of the possibility of achieving effective sterilization of such fluids outside the laboratory. Also, due to the relatively large scale of apparatus in use in blood and blood products processing laboratories, it has not been practicable to sterilize small quantities of such fluids such as single unit contributions in volumes of typically 250 to 500 mls, which may be required in the case of rare blood types, or particularly specialized products. Neither has there been any system available for rapid reliable sterilization of such small quantities of blood or blood products such as plasma out in the field more or less directly after collection of blood from a donor.

In more detail, conventional processing methods for virus inactivation in plasma and blood products usually require significant volumes of pooled product to be feasible for processing on an industrial scale. The use of such industrial scale equipment for processing of single donations of plasma or small pools of blood products (such as specific immunoglobulins) is not feasible, as the losses involved can be considerable. For example, a single donation of plasma from an individual donor typically has a volume of 250 ml and a double donation of plasma from an individual donor (eg obtained by plasmapheresis) will still only have a volume of about 500 ml. These volumes are of the same order of magnitude as the void volumes in industrial process scale equipment and substantial losses would accordingly be inevitable. Similarly, pools of specific antibodies for highly specialized applications (such as anti-rabies, anti-tetanus, anti-zoster and anti-rhesus) can range in volume from as little as 1L up to just a few tens of litres, again making them impractical for processing in large scale virus inactivation equipment.

Our own earlier European Patent No. 0 422 007 B discloses a relatively compact apparatus for sterilization of small quantities of blood or blood products inside a generally cylindrical bag or vessel by rolling it during irradiation thereof. The facilities for controlling the evenness of the radiation dosage applied throughout the fluid and minimizing damage from localized overheating and/or over-irradiation, are, however, somewhat limited.

It is an object of the present invention to avoid or minimize one or more of the above problems or disadvantages. It is a further object of the invention to provide an apparatus and method whereby microorganism inactivation without loss of product activity can be achieved without the need for adding or removing anything.

The present invention is based on our detailed investigations into the use of highly efficient mixing to overcome the twin problems of maximizing microorganism inactivation whilst minimizing product damage. An illuminated but intensely adsorbing fluid flowing in a pipe can be considered as having a thin "killing zone" at the outer surface of variable thickness and a major lumen occupying the remaining central volume which is not illuminated and therefore allows any microorganism e.g. virus to be preserved intact. By efficiently transporting fluid from the central "dark" zone to the outer "killing zone" and back again, a sufficiently large number of times and in a reliable and predictable manner, it should be possible to ensure that no virus escapes receiving a dose of illumination and that such dosing is uniform for all particles within the fluid. Since viruses are very small ($\geq 20$ nm) compared to the dimensions of a pipe it is easy for them to escape being uniformly irradiated and thus any mixing system has to be extraordinarily efficient at the microscopic level. We have found that static mixers can, but only when operated under certain clearly specified conditions, deliver such reliable and predictable performance. Such static mixers generally comprise a series of alternating left and right handed helical elements which divert the fluid flow left and right alternately and continuously re-divide the fluid differently into two halves. Such dividing operations can be repeated 'n' times by assembling a series of 'n' mixers in sequence such that the total number of subdivided volume elements is given by the expression $2^n$. This apparently simple approach can lead to astronomically large numbers of subdivided volume elements, eg. with 266 mixers one can obtain $10^{80}$ subdivided volume elements. Such a mixing system is convenient and reliable because it has no moving parts (other than the process fluid) and for labile biological fluids such as blood and plasma it minimizes the chances of damage caused by shear, heating or mechanical strain. Surprisingly, though, we have found that increasing the number of mixing elements per se is not sufficient by itself, reliably to inactivate virus in a predictable manner. Specifically, increasing the time a virus spends in the illuminated device will often not lead to a proportionate increase in the amount of virus killing. Instead, a residual amount of virus persists no matter how long the exposure time. This is a serious problem, (and is common to many different inactivation methods) as it not only makes the virus kill hard to predict but residual infective virus can be a serious liability in any blood product. Thus ideally one would seek to have a linear increase in virus kill with exposure time or light energy dose. It might be thought that increasing the intensity of the light source would be a solution to this problem. However such an approach has to date not been successful, and calculations based on the degree of penetration of light in strongly adsorbing fluids show that with eg. a "killing zone" of 0.05 mm thickness in a pipe of 20 mm diameter would require an increase in light intensity of 200 fold to illuminate the centre of the fluid lumen within the pipe. Such a source is not readily available and an additional problem with this approach is the increased risk of damage to labile molecules caused by the intense radiation at the surface of fluid and overheating. Surprisingly, we have found that it is possible to use low power light sources and still achieve good virus kills provided the mixing elements are operated within a clearly defined efficient flow regime. We have recently developed pilot and process scale devices (unpublished patent application PCT/GB99/03082) operating with pipes in the 4–25 mm diameter range. These are suited to treating pooled or manufactured blood products typically in the range of 1 L to 10,000 L, but because of their dead volume they are not suitable to treating individual donations of blood or plasma prior to pooling. Such donations typically have volumes in the range from less than 100 to 1000 ml or thereabouts and have not hitherto been amenable to any practical form of virus inactivation which is universally active against all viruses (It should be noted that the visible light methylene blue combination process marketed by Baxter under the trade name "PathInact" is only efficient against enveloped viruses).

Surprisingly, we have found that, depending on the fluid velocity or flow rate through the optical mixer device, there exist two distinct modes of operation: one which we describe as "efficient mixing" which exists above a certain fluid velocity or flow rate and the other which we describe as "inefficient mixing" which obtains below this velocity or flow rate. The transition from one to the other mixing regime occurs over a quite small range of fluid velocity or flow rate and can be pre-determined for a given combination of mixer diameter, tube length and feedstock fluid. Once determined, this efficient mixing regime can be reliably used to predict virus kill as a function of machine parameters and feedstock properties and this is a valuable property in validating a process or machine for the production of safe blood products. Surprisingly, we also find that as the fluid velocity or flow rate increases, the efficiency of virus inactivation (expressed as logs kill per second of exposure) is maintained constant or even increased whilst the degree of damage, (expressed as residual clotting factor activity recovered in plasma) decreases. Thus, unexpectedly, the control of flow rate not only improves the predictability of virus kill and the efficiency of virus kill but it also reduces the amount of product damage. This is a most valuable and surprising result, since blood products which are quite labile can now be subjected to efficient virus inactivation without the need for additives, and more specifically it is now possible to treat individual blood and plasma donations in a way that will significantly reduce the risk of disease transmission by known or unknown viruses. By this means we have found it possible to provide an apparatus with fluid pipes in the size range 1 to 4 mm id containing static mixers in an UV-irradiation zone which can be used for the effective treatment of individual donations of blood or plasma and small volumes of blood products in the range 100–1,000 ml. Thus the present invention provides a portable micro-organism inactivation system suitable for use with individual fluid units, comprising:

a casing mounting a UV radiation source, pump means, and releasable tube support means; and an elongate tube having:

a first portion with wall means of a UV-transparent material, and having an internal diameter of up to 4 mm, generally from 0.1 to 4 mm, preferably, from 1 to 4 mm, and containing a static flow mixing means extending therealong with a multiplicity of mixer elements for repeatedly subjecting a fluid flow therethrough, in use of the device, to a mixing operation comprising dividing and remixing of the fluid flow, in use of the system, a second portion interfaced with said pump means for pumping of fluid therethrough by said pump means in use of the system, upstream and downstream ends provided with first and second coupling means respectively for releasable fluid-tight connection of said elongate tube, in use of the system, to an individual fluid unit container of fluid to be treated and to a treated fluid container for receiving treated fluid, respectively, and having a sterile interior, said releasable tube support means being formed and arranged for releasably supporting said elongate tube so as to define a flow path extending therethrough which is substantially free of substantial discontinuities so as to avoid substantially turbulence in fluid flowing therealong in use of the apparatus, and with substantially only said first portion extending in close proximity to said UV radiation source within an irradiation zone thereof, and with said second portion interfaced with said pump means, whereby in use of the system substantially the whole of said individual fluid unit may be exposed to a similar micro-organism inactivating level of UV-irradiation, whilst minimizing damage to the desired components thereof, and then collected in a said treated fluid container.

In another aspect the present invention provides a method of inactivating micro-organisms in an individual fluid unit comprising the steps of:

providing an apparatus of the invention;

coupling an individual fluid unit container containing a said individual fluid unit and a container having a sterile interior for receiving treated fluid, to the upstream and downstream ends of the elongate tube; and pumping said fluid from said individual unit fluid container through said elongate tube into said container for receiving treated fluid while irradiating the first portion of said tube with said UV-radiation source.

Preferably the method of the invention includes the preliminary step of mounting a previously unused said elongate tube in said releasable tube support means.

It is also possible to use the present invention for the sterilisation of blood or blood products substantially directly following collection thereof from a donor. Thus an irradiation apparatus of the invention may be used in combination with a blood or blood product donation collection apparatus without the need for collection in a bag before sterilization, the donation being collected directly into a treated fluid bag or other container downstream of the inactivated tube first portion. Alternatively the irradiation apparatus could be used in combination with a plasmapheresis apparatus for sterilisation of the plasma extracted from a blood donation, prior to return of the donation residue (usually comprising primarily red blood cells) is returned to the body of the donor. It will of course be appreciated that where the donation collection apparatus itself normally includes a pump means, then one or other of the donation collection apparatus and inactivation apparatus pumps would normally be omitted. Where the latter pump is the one omitted, it would of course be necessary for the former to be configurable to provide a flow rate in the efficient mixing zone required by the present invention. Thus in a further aspect the present invention provides a method of obtaining a sterilized blood or blood product donation from a donor which method comprises the steps of:

providing a blood or blood product donation collection apparatus having a sterile, blood or blood product receiving, container, and a microorganism inactivating apparatus of the present invention;

coupling the upstream and downstream ends of the elongate tube of the microorganisms inactivating apparatus in-line with the blood or blood product donation device upstream of said blood or blood product receiving container; and pumping said fluid from the donor through said elongate tube into said, blood or blood product receiving, container while irradiating the first portion of said tube with said UV irradiation source.

It should also be noted that the methods and apparatus of the present invention are also useful for the sterilisation of a wider range of fluids which may require treatment in relatively small volumes outside of dedicated sterilisation plant. Such fluids may on the one hand include blood or blood product obtained from transgenic animals, other biological fluids obtained using biotechnological procedures such as genetic engineering, and on the other hand cutting fluids used in machine tools such as lathes etc for drilling, milling, cutting and like operations, and the present invention encompasses the application of the novel methods and apparatus disclosed herein, to these also.

Thus by means of the present invention it is possible to achieve high rates of microorganism inactivation with minimal product damage on small volumes of blood or blood products, in a simple and economic matter outside of dedicated processing laboratories. It is a further advantage of the present invention that products which have hitherto not been amenable to virus inactivation can now be processed with minimal volumetric losses, for example the void volume in the system and apparatus of the present invention can be as little as 1–10 ml which reduces volumetric losses to the order of a few percent or less in the case of small quantities of fluid. Yet another advantage of the proposed device and process is that the costs associated with the processing step and equipment are minimal, making it feasible to process raw material such as plasma in single or double donation volumes without major added cost. The light source and pump use power of only a few watts and the illuminated mixer element is sufficiently small and composed of mass produced plastic items (which are readily assembled by eg a heat shrinking step) to permit them to be used once only and disposed of after use. Furthermore, the disposable element contains no sharp metal or glass components which makes it safe to dispose of even when in contact with potentially infectious material. It is a further advantage of this device that, following use, the disposable element will have been sterilized, thus further reducing risks of infection.

Various pump means may be used in accordance with the present invention. In order to minimize the risks of contamination there is preferably used a pump of a type in which the pump motor and drive transmission components are isolated from the fluid. Thus for example, there may be used a diaphragm pump in which the second portion of the tube is connected via one-way inlet and outlet valves to a chamber having a diaphragm wall portion which is reciprocably displaceable by a pump motor and reciprocating drive output member inter engaged with the outside of the diaphragm wall. In this arrangement only the interior of the chamber and the valves need to be sterile. Most conveniently though there is used a peristaltic pump in which a rotary drive output member with a series of circumferentially distributed transverse rollers or bars is used to repeatedly apply a constriction to a length of the tube corresponding to the second portion thereof which constriction advances along the length of said second tube portion wherein the pump motor and drive transmission components are entirely isolated from the fluid flow through the second portion of the tube which can be integrally formed with other parts of the elongate tube. This simplifies replacement of the tube after each use of the apparatus and minimizes the number of components requiring to be replaced after each use. Nevertheless it will be appreciated that other kinds of pumps could in principle be used provided that all fluid-contacting surfaces are sterile, the design of fluid flow passages and fluid flow impeller means is such as to substantially avoid turbulence in the fluid flow, and the cost of the pump (or relevant components thereof) permits disposability thereof after a single use.

As noted hereinabove we have found that by suitable control of the fluid flow rate through the first portion of the tube, it is possible to achieve high rates of microorganism inactivation whilst minimizing damage to the desired components of the fluid. Thus in a particularly preferred aspect of the present invention, the pump means is formed and arranged so as to provide a fluid flow rate at a fluid flow rate not less than a minimum flow rate corresponding to a maximum fluid residence time (within said irradiation area) required for efficient mixing as indicated by the maintenance of a substantially linear relation between log kill and residence time which obtains above said minimum flow rate and at a fluid flow rate not greater than a maximum fluid flow rate corresponding to a minimum residence time in said irradiation area required for effective inactivation of a said contaminating micro-organism by providing a desired log kill of said micro-organism, (preferably not less than that required for a 4 log kill of said contaminating micro-organism, in general not less than 1 second, for example, not less than 10 seconds), wherein said minimum residence time in said irradiation area is defined in accordance with the following relationship:

$$\log 10 \text{ kill} = K \times \text{Flux} \times \text{Residence time}/OD \times \text{Tube Radius}$$

wherein Flux indicates the amount of UV radiation incident on the passage containing the fluid flow in the irradiation area, in mW cm$^{-2}$; OD is the Optical Density (absorbance of 1 cm) of the fluid at the wavelength in the region where substantial virus inactivation takes place (typically in the range 250 to 280 μm); K is an empirically derived constant; and Tube Radius is the internal radius of the vessel in the irradiation area, in cms, whereby in use of the apparatus substantially the whole of the fluid may be exposed to a similar micro-organism inactivating level of UV-irradiation whilst minimizing damage to the desired component(s) of the fluid.

It will be appreciated that this is a modified form of the Bunsen-Roscoe reciprocity law, derived for microbial killing on a surface, which states that LRV=constant×light flux×exposure time. The additional terms needed to cope with a flowing fluid in a thick adsorbing layer are the optical density of the process fluid and the pipe radius. This "ideal" relationship predicts a linear dependence of virus kill on residence time and this is only true in the "efficient mixing" zone indicated (for a particular case) in FIG. 3, in which zone log kill is linearly related to residence time. At flow rates of less than a defined amount, the mixing becomes inefficient and the above simple relationship does not obtain. Thus it is necessary to operate in the "efficient mixing" regime in order to be able to predict the virus kill in response to equipment and process variables. The value of the composite constant K is most easily determined empirically for a model virus such as bacteriophage Øx174. Once this value is determined, the value can be estimated for other viruses using the published absolute/relative values for other micro-organisms relative to bacteriophage Øx174. The value of the effective lamp power (Flux) is most easily determined by actinometry using the below described actinometry system.

The elongate tube may be a simple continuous length of tube having the UV-transmissibility required for the first portion thereof and the physical characteristics e.g. flexibility required of the second portion for effective interfacing with a suitable pump drive mechanism such as, for example, a peristaltic pump. More commonly though the elongate tube may be made of discrete sections of different materials with different properties optimized to a greater or lesser extent for the respective requirements of the first and second portions, and one or more connector sections used for interconnecting these to each other (albeit that one or more of these connector sections and/or the coupling means may be formed integrally with one or other of the first and second tube portions).

The first portion of the tube has an internal diameter of up to 4 mm and preferably has a series of helical static mixer elements disposed within the lumen. Advantageously there is used a static flow mixing means in the form of an elongate screw threaded member having alternate mixer elements of opposite handed screw thread. Static flow mixers of this kind have been known and used for many years for various purposes such as food and chemical product manufacture, and are commercially available from inter alia Chemineer Inc of North Andover, Mass., USA under the Trade Name KENICS KM and Liquid Control Ltd of Wellingborough, England under the Trade name POSIMIXER, and provide very intensive mixing as a result of a combination of a number different mixing effects comprising flow division through repeated division of previously divided streams thus creating a geometric progression of flow division according to the formula D=2n where D is the number of flow divisions and n is the number of mixer elements; flow reversal whereby the direction of rotation about the longitudinal axis of the mixer is reversed at each mixer element (clockwise—anti-clockwise—clockwise etc.); radial mixing resulting from flow reversal and flow inversion which occurs when fluid close to the centre of each of the separate flows at a mixer element of the device is driven radially outwardly when it encounters the edge of a new mixer element; and resulting inhibition of axial differentiation (corresponding to establishment of axial flow profiles).

The first portion of the tube is positioned close to the surface of a UV-radiation source, preferably one emitting UV-C radiation, such as a low pressure mercury discharge lamp emitting light energy primarily in the 254 nm line. The material of the tube is generally chosen so that it has a reasonable transmissibility to 254 nm radiation. Suitable commercially available materials typically transmit 50 to 85% of such radiation. The thickness of the tube wall can also be varied and chosen for a given material so as to be in this range of transmission, eg. a 1 mm thick wall silica tube or a 0.2 mm thick wall pTFE tube. The length of the first portion of the tube is conveniently chosen to approximately correspond to the length of the UV-radiation source. Various suitable UV lamp sources may be used in the system and apparatus of the present invention. In general it is preferred to use a relatively compact low power UV source. In the case of a Phillips PLS 11W TUV lamp the length is 19 cm whereas for a Phillips 15W TUV lamp this is 45 cm. More than one length of tube can be disposed in the irradiation zone adjacent the UV-radiation source lamp so that the first portion comprises a plurality of lengths of substantially UV transparent tubing containing static mixer elements, which lengths are inter connected in series by flexible or rigid connecting sections which need not be necessarily UV transparent.

By using relatively small low power UV radiation sources, it is possible to use portable power sources such as batteries, conveniently rechargeable batteries and/or solar cells, manually driven dynamos, conveniently with coiled spring, flywheel etc energy storage devices. Such means enhance still further the portability and in-the-field capability of the system and apparatus which make it particularly suitable for emergency, disaster relief, and like applications. Nevertheless the UV radiation sources and pump means may also be of mains powered type for applications where mains electricity is available and/or for use together with portable generators.

The "efficient mixing" regime and the minimum desirable flow rate may be readily determined by means of simple experimental procedures as further described hereinbelow. A quantity of fluid of the type requiring to be treated, spiked with a marker virus (eg. bacteriophage Ø×174) to a high titre (typically 1:$10^8$) is pumped through a given diameter and length of the tube first position while it is being irradiated. The flow rate is varied from a low value eg. 2 ml/min to a high value eg. 100 ml/min using suitable flow rates in between these limits. Samples of irradiated feedstock are collected for each flow rate and the degree of virus inactivation is plotted against the residence time (Rt) of particle within the mixed illuminated zone. The value of Rt is most easily derived by measuring flow rate and dividing by the predetermined mixed illuminated void volume. When plotted in this way a characteristic shape of curve is obtained (see FIG. 3), figures in parentheses indicate the flow rate in ml/min at each data point. For shorter residence times (i.e. for faster flow rates), the amount of virus kill increases linearly from the origin and rises steeply, however at a certain narrow range of flow rate (residence time) the virus kill ceases to increase and the amount of residual surviving virus remains constant despite increasing residence time (and hence increasing doses of radiation). The initial (steep) slope of the curve represents the region of "efficient mixing" whereas the later flat part of the curve represents the region of "inefficient" mixing. The transition between the two indicates the flow rate below which the device should not be operated with that feedstock and that tube-static mixer combination. This observation has several important and valuable implications. Firstly, it is clear that to scale-up the dose of radiation it is generally better to increase the length of pipe (or use multiple passes) rather than to decrease the flow rate (and increase the residence time). Secondly, once a particular feedstock and mixer element size has been chosen, a minimum flow rate for this combination must always be respected to achieve high efficiency of virus inactivation. Thirdly, because the steeper part of the curve is substantially linear, it allows for more reliable prediction of virus kill when changing process parameters such as OD, flow rate, lamp power, number of lamps, pipe material and thickness, and pipe length and diameter e.g. in order to easily accommodate variations in OD between individual donations and also allows for more reliable design of apparatus to yield a given target level of virus inactivation. An added advantage of operating in the "efficient mixing" region is that it minimizes damage to labile components at the surface of the tube caused by over-exposure to excessive radiation and minimizes local overheating by efficient and rapid transport of heat away from the tube wall and into the cooler bulk of the fluid.

Once the minimum flow rate is known, the desired virus kill can be achieved by either increasing the length of optical mixer pipe and/or by passing the fluid through the device several times. Scaling up the length of pipe is primarily limited only by the back pressure caused by the number of mixer elements and the viscosity of the feedstock. When the back pressure exceeds the desirable limit set by the pump, tubing and connectors, then greater virus kill can still be obtained by using the multiple pass strategy, ie the batch of fluid to be processed can be passed through more than once. Generally however, as plasma has quite a low viscosity there may be used a tube length such that a single pass is sufficient to give adequate virus inactivation and this is very much preferred in view of greater ease and simplicity of operation and greater safety and reliability.

The degree of labile plasma factor damage can be estimated by assaying for individual coagulation factors using assays, well known to those skilled in the art. Such factors include fibrinogen, factor V, factor VIII, factor IX, factor X and factor XI. The extent of retention of these factors for different degrees of exposure to radiation can be used to set an upper limit for the amount or radiation dose (fluence or mJ/$cm^2$) that is acceptable. (Where the flux of the lamp is known in mW/$cm^2$, the fluence, or work done per unit area of the device can be calculated by multiplying the residence time in seconds and the lamp flux, the units of fluence are thus mJ/$cm^2$. In many cases, it is more realistic to calculate the work done on the process fluid as Joules per ml of product. To convert from fluence (in mJ/$cm^2$) into Joules/ml a factor of $2/r$ is used where 'r' is the pipe radius in cm, a factor of $1/1000$ is used to convert mJ into Joules, and a correction factor kA/V is also required to convert for the proportions of surface area and volume occluded by the presence of the mixer elements within the pipe. This factor is typically 1.275 for the case of a 3 mm static mixer of preferred type described hereinbefore. Thus the overall conversion factor is $2/r \times 1/1000 \times 1.275 = 0.017$). Surprisingly, we have found that damage to labile factors can be minimized by operating at or above the minimum flow rate for "efficient mixing" and that additives are not required to protect the labile factors from radiation damage. (Nevertheless if it is required to employ an additive for some reason, this can also be done without departing from the scope of the present invention, albeit that this is less preferred). A likely mechanism for this self-protection is that "hot spots" at the wall of the tube are minimized and no molecule is subjected to any greater dose of radiation than any other. Thus, operation in the region of "efficient mixing" simultaneously enhances virus kill and minimizes protein damage—probably by the same mechanism of extremely uniform mixing at the microscopic level.

It is often desirable to measure the actual dose of light energy adsorbed by a flowing fluid within the lumen of the optical elements. Although this can be estimated from the known power of the lamp and the residence time in the device a number of confounding factors seriously limit the accuracy of this approach including heterogeneous distribution of light, variable transmission of the wall of the optical element pipe and scattering and reflections. Thus a more direct approach is desirable, however it is not feasible to place electronic sensors within the lumen of the small pipe diameters used, nor do they accurately reproduce the extremely heterogeneous nature of the adsorption process caused by self adsorption of the feedstock.

We have found that appropriately formulated sodium iodide can be useful as an actinometric reagent to measure the absolute and relative amounts of light-work done on the process fluid. Such a reagent typically consists of 1% w/v NaI in 20 mM Tris buffer pH 7.50+0.01. The accurate adjustment of pH is important as this controls the sensitivity of the reagent. At acid pH values the reagent becomes more sensitive and at alkaline pH values it becomes less sensitive. The reagent can be stored for several weeks at 20° C. in a dark cupboard. In order to provide absolute units (J/$cm^3$) of work done by light energy adsorbed per unit volume of process fluid, the reagent was placed in a 10×10 mm cross section silica cuvette at a distance of 50 mm from a source of UV-C and at the same distance an integrating UV-C electronic power sensor was also positioned. The reagent was stirred vigorously with a magnetic stirrer whilst illuminated with UV-C light for varying periods of time. The visible yellow colour due to iodine formation was quantitated by spectrophotometry in a 1 cm path length cuvette at 352 nm and plotted against the integrated value of the meter display in mJ/$cm^2$. For a 1 cm square cross section cuvette, the numerical value of mJ/$cm^2$ is the same as that value in mJ/cm$^3$ because 1 cm$^2$ of surface area corresponds to 1.00 ml of solution. The results of this absolute calibration curve are plotted in FIG. 4. If relative rather than absolute comparisons of work done on the process fluid are adequate, eg. to validate that the equipment is delivering the same light dose on successive occasions, then it is feasible to just quote the absorbance value A1 cm obtained with the actinometry reagent when pumped through the device at the same flow rate as the process feedstock. For a given lamp/pipe combination, it is possible to work backwards from the observed actinometry absorbance values, the interpolated work density (in J/ml) and the residence time (Rt) to derive an apparent or effective lamp power in mW/cm$^2$, which can be useful in monitoring lamp performance or designing new equipment to give a particular numerical value of virus kill. In particular a knowledge of the effective lamp power in absolute units is highly desirable to insert into an equation for calculating or predicting virus kill. Such an absolute value of the effective lamp power cannot be measured directly by electronic sensors because of the above mentioned confounding factors (heterogeneity, transmission losses, reflection and refraction). An additional advantage of the iodide based actinometric reagent is its insensitivity to visible and near UV light (the absorption of the reagent is essentially nil above a wavelength of 300 nm) in contrast the reagent adsorbs strongly at 254 nm., having an absorbance A1 cm of about 20 AU, and in this respect it is a useful analogue of any strongly adsorbing process fluid, mimicking the strongly heterogeneous adsorption process in a thin layer at the surface of the optical pipe.

Further preferred features and advantages of the present invention will appear from the following detailed description given by way of example of a preferred embodiment illustrated with reference to the accompanying drawings, and from the following examples of the use and calibration of this embodiment.

Figure 1:
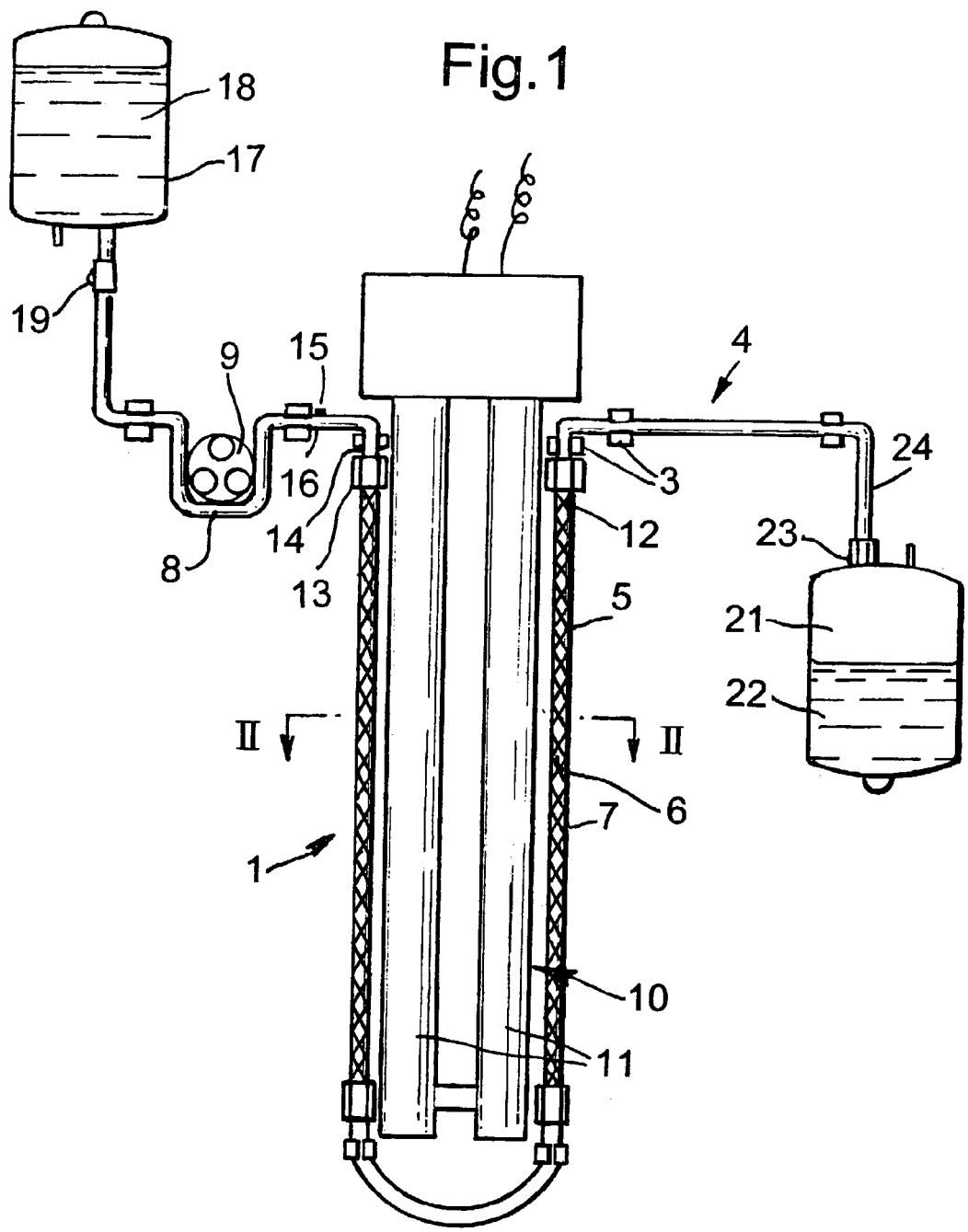
FIG. 1 is a schematic side elevation of an irradiation system of the invention (with the first portion of the tube shown displaced for greater clarity)
Figure 2:
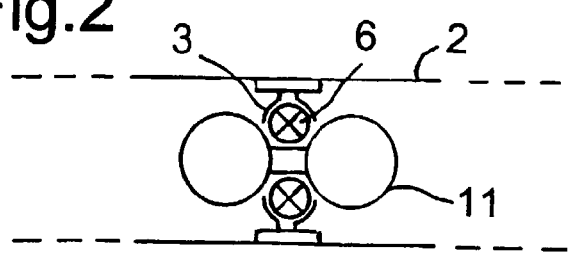
FIG. 2 is a detail cross-sectional view of the system of FIG. 1.

FIG. 1 shows an irradiation system of the invention 1 comprising a casing 2 (see FIG. 2) having a plurality of tube support clips 3 (only some shown) for releasably securing an elongate tube 4 having a first portion 5 including two lengths of UV transparent tubing 6 containing static mixer elements 7, and a second portion 8 supported in engagement with a peristaltic pump device 9. (Note—the two lengths of UV transparent tubing 6 are actually disposed as shown in FIG. 2 so as to maximize the UV radiation dosage incident thereupon and have been drawn out of position in FIG. 1 solely for the purposes of greater clarity). In more detail a series of eight 3 mm diameter static helical mixer mouldings (MeterMix Company of wellingborough, England Part No: MM0308) having a total assembled length of 190 mm was mounted within a length of heat shrinkable PTFE tubing 6 (Adtech Part No: FHS 2.7), wall thickness 0.2 mm; ID before shrinking 3.6 mm; ID after shrinking 3.0 mm, to provide the first tube portion 5. The actual length of tubing after shrinking was 265 mm which allows for connections at either end outwith a central irradiated mixing portion. Each mixer element moulding consists of 8 individual helical elements, giving a total of 64 binary mixing/dividing elements or $2^{64}$ subdivided volume elements ie. $1.8 \times 10^{19}$. The internal mixed irradiated volume (Vo) was determined to be 0.94 ml by injecting water and weighing. The characteristic dimension of the final subdivided volume element is thus defined as $^3\sqrt{Vo/2^{64}}$ or $^3\sqrt{0.94/1.8 \times 10^{19}} = 4 \times 10^7$ cm or $4 \times 10^{-9}$ m or 4 nm, which is significantly smaller than the target viruses of 20 nm diameter.

This first tube portion 5 is mounted using release tube support clips 3 in close proximity to a UV source 10 in the form of a Phillips PLS11W-TUV low pressure mercury discharge lamp which consists of two lamp tubes 11 joined together in a 'U'-shaped format with a central groove at either side which provide convenient mounting positions for the first portion parallel to the lamp tubes. The length of the lamp is 190 mm which dictates the irradiated length of the first tube portion sections 6. (The effective length of the irradiated first portion being approximately 2×190 mm). The upstream and downstream ends 12 of the first tube portion 5 are conveniently provided with male or female Luer type fittings 13 which allow ready connections to existing medical grade sterile tubing, transfer packs, pump elements etc. Other suitable modes of sterile connecting device will be apparent to those skilled in the art. A Gilson Minipuls III pump (available from Anachem company of Luton, England); having a flow rate adjustable within the range from 1 to 100 mls/min (for a tube i.d. of around 3 mm) engaging a 3 mm i.d. tube second portion, is conveniently used as the peristaltic pump 9. Conveniently also temperature sensing probes 14 are provided at the inlet and outlet ends 12 of the first portion and a pressure sensor 15 at the outlet 16 of the pump 9 for the purposes of monitoring the operation of the system in the course of establishing its performance parameters although these would not be necessary during normal use of the apparatus. The second portion 8 of the tube 4 was a flexible material such as Marprene (Trade Name) (available from Watson-Marlow of Falmouth, England) commonly used in peristaltic pumping situations. It will of course be appreciated that for a single-use application such as is contemplated by the present invention, a tube material with significantly shorter wear life—such as silicone, polyurethane, or PVC, would be quite acceptable. A first bag 17 containing freshly collected plasma 18 is connected using a Luer type coupling 19 provided at the upstream end 20 of the tube 4, and a sterile second bag 21 for receiving the sterilized plasma 22 was connected in similar manner using a Luer coupling 23 at the downstream end 24 of the tube 4. Once the contents 18 of the first bag 17 had been processed the second bag 21 containing the sterilized plasma 22 is detached from the tube 4 and sealed. In normal use the complete tube 4 is then removed from the releasable clips 3 together with the first bag 17 for safe disposal, and a fresh tube 4 mounted in position and a new bag of plasma requiring treatment may then be connected thereto, along with a fresh sterile bag for collection of sterilized plasma.

EXAMPLE 1

Measurement of Damage to Plasma Components, and Actinometry Measurement

Figure 4:
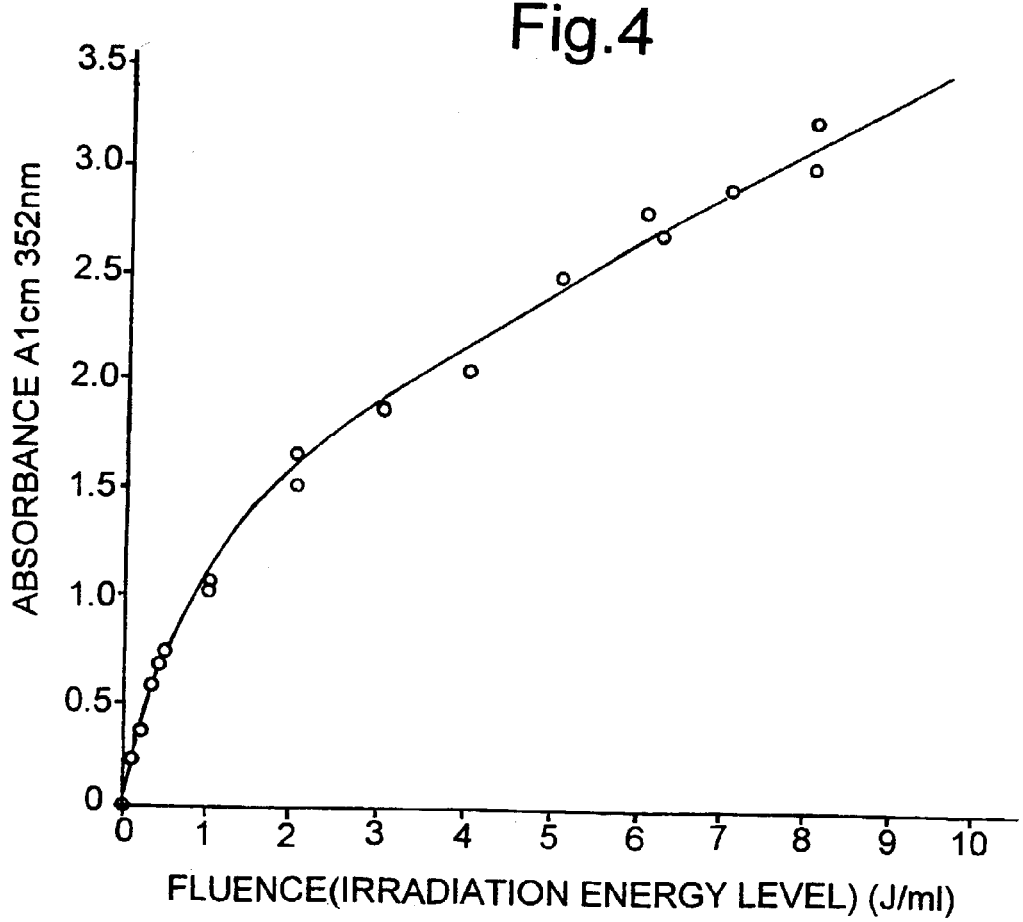

Bags of plasma (150 mls) were connected to the upstream end of the elongate tube of an apparatus as illustrated in FIGS. 1 and 2 but with a single UV transparent tube length 6 in the first tube portion 5. Plasma was pumped through the apparatus at various flow rates and the temperature rise of the feedstock, back pressure and flow rate were monitored. Samples of plasma at each flow rate were collected and subsequently analyzed for fibrinogen and coagulation factors V, VIII, IX, X and XI. After flushing with saline to clean the device, an iodide based actinometric reagent as described hereinbefore was pumped through the device at the same pump settings and the absorbance values A1 cm were determined after holding the samples for 1 to 2 hours. The physical values obtained are summarized in Table 1 and the biological assay values are summarized in table 2 From table 1 it will be seen that the maximum temperature rise seen was 20° C. at a residence time of 28.1 seconds. Therefore assuming a feedstock input temperature of 20° C., this would raise the product to 40° C. which might be considered too high for labile coagulation factors, so a residence time of 14.3 seconds, giving a temperature rise of 14.7° C. and a final product temperature of 35° C. would be acceptable, being within the physiological range. The pressure drop ranged from 1.3 to 3.76 psi which is low and comfortably within the limits for conventional peristaltic pumps and tubing connectors. The actinometry absorbance values show a smooth increase with exposure time, and can be interpolated in a calibration curve (see FIG. 4) to provide absolute values of the irradiation energy level in Joules/ml and by means of a constant for the apparatus, mentioned above, can be converted into fluence or mJ/cm$^2$ values. Both these sets of data can in turn be used to calculate the apparent lamp power (via the individual values of the residence time), which in this case is approximately 16 mW/cm$^2$.

The bioassay data in table 2 show that plasma coagulation factors have varying susceptibility to UV-C induced damage.

The sequence of increasing sensitivity to damage was factor V<factor VIII<fibrinogen<factor IX<factor XI. Thus factor XI would appear to be the most sensitive indicator of damage, and if a practical limit of >/=0.70 international units per ml of product were desired, then the conditions of using pump setting P3 should not be exceeded (ie a residence time of 5.81 seconds or fluence of 165 mJ/cm$^2$). Under these conditions, the yield (undamaged) of other factors would then be factor V 88%, factor VIII 84%, fibrinogen 77%, and factor IX 74%.

EXAMPLE 2

Inactivation of Virus in Plasma

Figure 3:
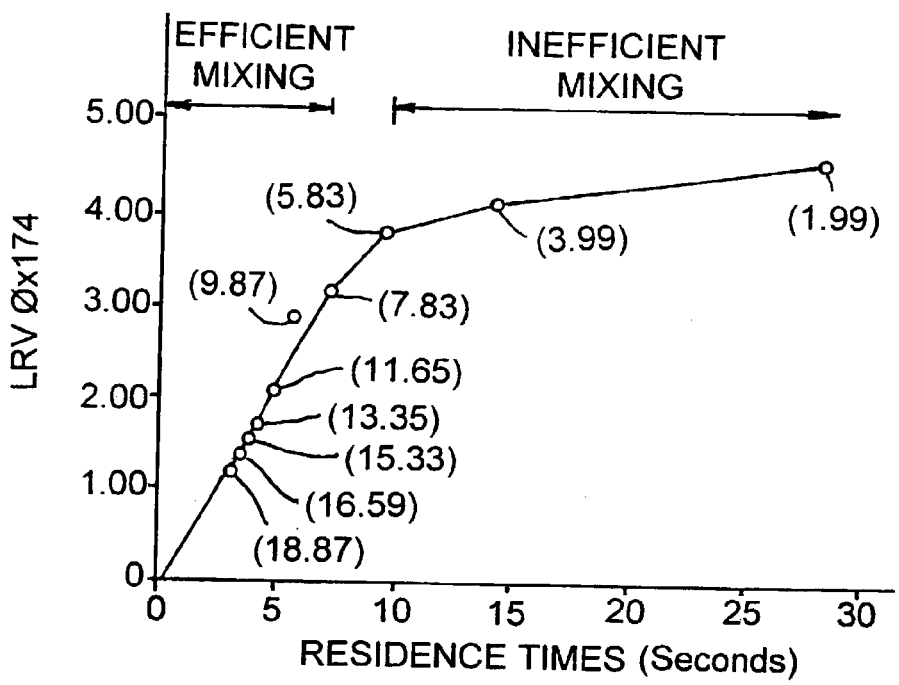
FIGS. 3 to 6 are graphs of the measurements obtained in the following examples.

The procedure as described in example 1 was again used, except that the plasma feedstock was spiked with the bacteriophage virus Phi-X 174 to a titre of 1:10$^8$, and the plasma was pumped through the device at flow rates ranging from 2 ml/min to 20 ml/min. The optical density (OD) of the feedstock was measured (after diluting ten-fold for measurement purposes) and was calculated back to be 23.38 AU at 254 nm in a 1 cm cuvette. The titre of the virus in the irradiated plasma was determined by serial dilution on bacterial plates of $E. coli$ and the decrease in log titre was calculated to quantitate the value of the LRV (log reduction value). The various measurements recorded are summarized in Table 3 and are in general rather similar to the data in Table 1. The virus kill (last column of table 3) was plotted against the residence time (third column of table 3) in FIG. 3, the figures in parentheses at each point plotted being the flow rate for that measurement. Plotting log kill against flow rate is less informative than plotting against residence time. The latter plot clearly shows (FIG. 3) that at flow rates above 8 ml/min the slope of the virus kill versus residence time is 0.45 log kill units per second whilst at flow rates below 6 ml/min the kill is much less efficient with a slope of only 0.04 log kill units per second, ie a reduction in efficiency of around ten fold. From the data of table 3 and FIG. 3 we conclude that it is necessary to operate above a minimum flow rate which can be deduced experimentally for a particular mixer diameter and feedstock composition from a plot of log kill versus residence time.

EXAMPLE 3

Inactivation of Virus Using Increased Irradiation Flow Path Length

Figure 5:
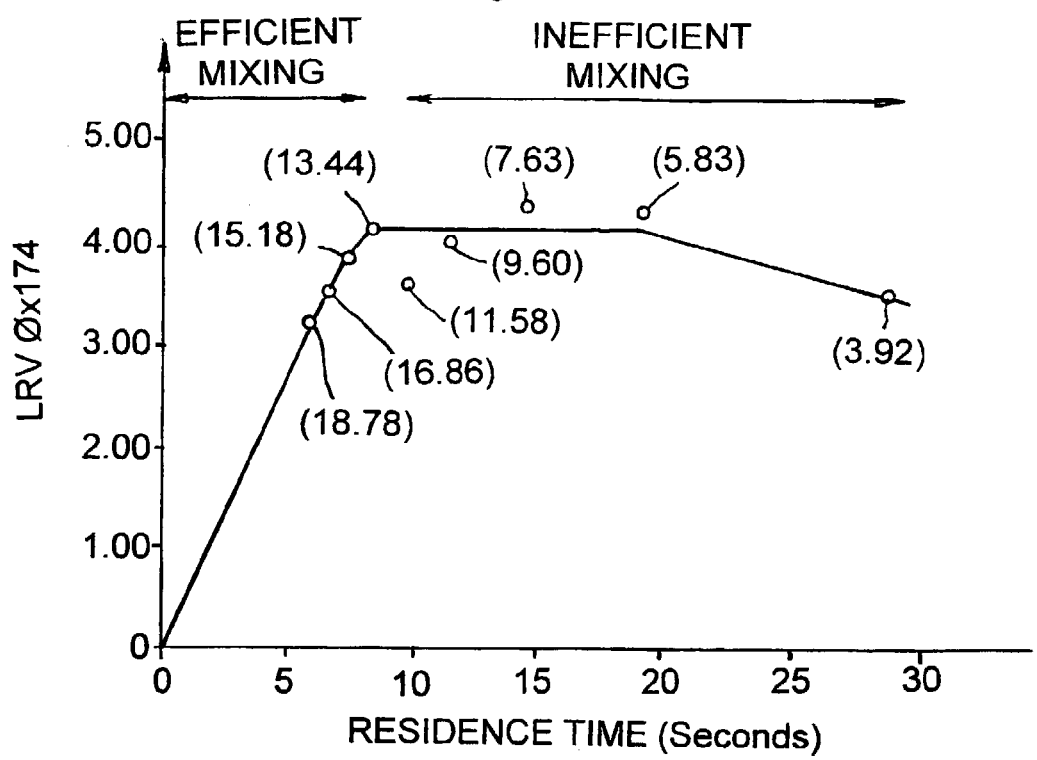

The procedure as described in example 1 was followed except that two lengths of UV transparent tube were placed at opposite sides of the light source and connected in series such that the mixed irradiated path had a total length of 380 mm with 16 moulded mixer elements having a total of 128 binary dividing/mixing operations and a void volume of 1.88 ml. This would provide a total of 2$^{128}$ or 3.4×10$^{38}$ subdivided volume elements, having a characteristic dimension of 1.8×10$^{-6}$ nm or some seven orders of magnitude smaller than a virus. The feedstock was plasma spiked with bacteriophage phi-X 174 to a titre of around 10$^8$; after diluting ten-fold the (original) optical density was calculated to be 23.5 at 254 nm in a 1 cm cuvette. The flow rate was varied from 3.9 ml/min to 18.8 ml/min giving residence times from 6 to 28 seconds. The numerical results are summarized in table 4 and the log kill versus residence time figures are plotted in FIG. 5, the figures in parentheses are the flow rates for each data point. Examination of the plot in FIG. 5 shows that the minimum flow rate for efficient mixing, as judged by the steepest part of the curve in this case was around 13 ml/min, with a corresponding slope of 0.4 3 logs kill per second of residence time. Thus doubling the length of pipe relative to example 2 has resulted in double the flow rate (and consequently productivity) for the same amount of virus kill whilst maintaining the efficiency (slope) at 0.43 logs/sec. This demonstrates that it is feasible to scale up productivity and maintain virus kill by increasing the length of illuminated mixing pipe. In contrast, reducing the rate of flow below a critical value will offer no benefits in terms of virus kill or productivity. Furthermore the data of table 4 show that both backpressure and temperature rise can be maintained within acceptable limits.

EXAMPLE 4

Inactivation of Virus Using Increased Flow Rate

As for example 3 except that the flow rate used was varied in the range 20 to 100 ml min, and the plasma (spiked with bacteriophage phi-X 174) had an original optical density of 24.32 at 254 nm in a 1 cm cuvette. The numerical data are summarized in table 5 and the values for log virus kill are plotted against residence time in FIG. 6, the figures in parentheses are the flow rates at each data point. The data in table 5 show that even at these high flow rates, back pressure is still well within the practical limit for operating with peristaltic pumps and tubing, and the temperature rise is small. Actinometry data were consistent with an effective lamp power of 17 mW/cm$^2$.

Figure 6:
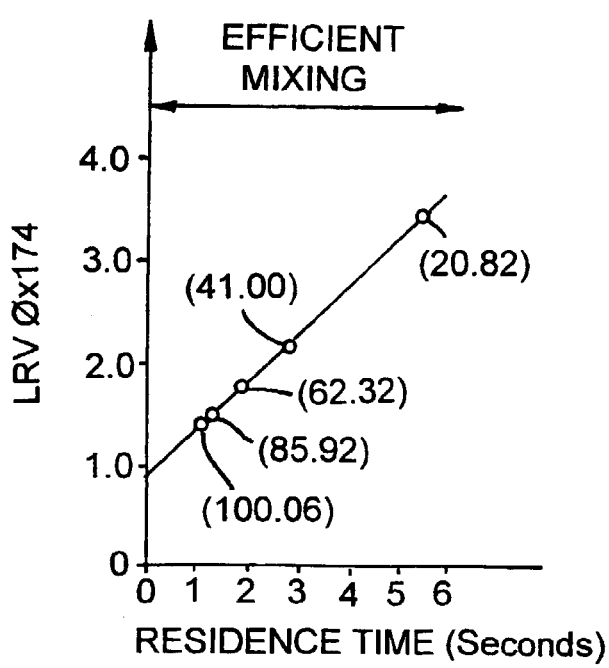

The virus log kill data from table 5 are plotted in FIG. 6 as a function of residence times, and show that compared to the lower flow rates in example 3 and FIG. 5, the faster flow rates now ensure that all data points fall on the linear and steepest part of the curve which corresponds to the region of efficient mixing. Furthermore the efficiency, expressed as the slope of this line is 0.46 logs per second, thus it is maintained essentially identical to that obtained in examples 2 and 3. We consider that this is a valuable attribute of working in the region of efficient mixing, above the minimum flow rate, since it allows for accurate prediction of virus kill and scaling up performance by increasing pipe length.

The invention claimed is:

1. A portable micro-organism inactivation system suitable for use with individual fluid units, comprising:
   a casing mounting a UV radiation source, pump means, and releasable tube support means; and an elongate tube having: a first portion with wall means of a UV-transparent material and having an internal diameter of around 3 mm, and containing a static flow mixing means extending therealong with a multiplicity of mixer elements for repeatedly subjecting a fluid flow therethrough, in use of the system, to a mixing operation comprising dividing and remixing of the fluid flow substantially without inducing turbulence in said fluid flow, in use of the system; a second portion interfaced with said pump means for pumping of fluid therethrough by said pump means in use of the system; upstream and downstream ends provided with first and second coupling means respectively for releasable fluid-tight connection of said elongate tube, in use of the system, to an individual fluid unit container of fluid to be treated and to a treated fluid container for receiving treated fluid, respectively, and having a sterile interior,
   said releasable tube support means being formed and arranged for releasably supporting said elongate tube so as to define a flow path extending therethrough which is substantially free of substantial discontinuities so as to substantially avoid turbulence in fluid flowing therealong in use of the system, and with substantially only said first portion extending in close proximity to said UV radiation source within an irradiation zone thereof, and with said second portion interfaced with said pump means, said pump means being provided with a flow controller formed and arranged for limiting the flow of said fluid through said tube between predetermined flow rate limits so that in use of the system substantially the whole of said individual fluid unit is exposed to a similar micro-organism inactivating level of UV-irradiation, whilst minimizing damage to the desired components thereof, and then collected in a said treated fluid container.

2. A portable micro-organism inactivation system suitable for use with individual fluid units, comprising:
   a casing mounting a UV radiation source, pump means, and releasable tube support means; and an elongate tube having: a first portion with wall means of a UV-transparent material, and containing a static flow mixing means extending therealong with a multiplicity of mixer elements for repeatedly subjecting a fluid flow therethrough, in use of the system, to a mixing operation comprising dividing and remixing of the fluid flow substantially without inducing turbulence in said fluid flow, in use of the system; a second portion interfaced with said pump means for pumping of fluid therethrough by said pump means in use of the system; upstream and downstream ends provided with first and second coupling means respectively for releasable fluid-tight connection of said elongate tube, in use of the system, to an individual fluid unit container of fluid to be treated and to a treated fluid container for receiving treated fluid, respectively, and having a sterile interior,
   said releasable tube support means being formed and arranged for releasably supporting said elongate tube so as to define a flow path extending therethrough which is substantially free of substantial discontinuities so as to substantially avoid turbulence in fluid flowing therealong in use of the system, and with substantially only said first portion extending in close proximity to said UV radiation source within an irradiation zone thereof, and with said second portion interfaced with said pump means, said pump means being provided with a flow controller formed and arranged for limiting the flow of said fluid through said tube between predetermined flow rate limits so that in use of the system substantially the whole of said individual fluid unit is exposed to a similar micro-organism inactivating level of UV-irradiation, whilst minimizing damage to the desired components thereof, and then collected in a said treated fluid container, wherein said static flow mixing means comprises a series of 3 mm diameter static helical mixer moldings and said first portion of said elongate tube is made of heat shrinkable PTFE tubing which has been shrunk to have an internal diameter of 3.0 mm.

3. A portable micro-organism inactivation system suitable for use with individual fluid units, comprising:
   a casing mounting a UV radiation source, pump means, and releasable tube support means; and an elongate tube having: a first portion with wall means of a UV-transparent material, and containing a static flow mixing means extending therealong with a multiplicity of mixer elements for repeatedly subjecting a fluid flow therethrough, in use of the system, to a mixing operation comprising dividing and remixing of the fluid flow substantially without inducing turbulence in said fluid flow, in use of the system; a second portion interfaced with said pump means for pumping of fluid therethrough by said pump means in use of the system; upstream and downstream ends provided with first and second coupling means respectively for releasable fluid-tight connection of said elongate tube, in use of the system, to an individual fluid unit container of fluid to be treated and to a treated fluid container for receiving treated fluid, respectively, and having a sterile interior,
   said releasable tube support means being formed and arranged for releasably supporting said elongate tube so as to define a flow path extending therethrough which is substantially free of substantial discontinuities so as to substantially avoid turbulence in fluid flowing therealong in use of the system, and with substantially only said first portion extending in close proximity to said UV radiation source within an irradiation zone thereof, and with said second portion interfaced with said pump means, said pump means being provided with a flow controller formed and arranged for limiting the flow of said fluid through said tube between predetermined flow rate limits so that in use of the system substantially the whole of said individual fluid unit is exposed to a similar micro-organism inactivating level of UV-irradiation, whilst minimizing damage to the desired components thereof, and then collected in a said treated fluid container, wherein said first portion has an internal diameter of from 1 mm to around 3 mm.

4. A system as claimed in claim 3, wherein the system has a void volume of from 1 to 10 ml.

5. A system as claimed in claim 3, wherein the pump comprises a pump motor and drive transmission components which are isolated from the fluid to be treated.

6. A system as claimed in claim 3, wherein said pump comprises an impeller disposed within said elongate tube, and drive means formed and arranged for driving said impeller within the elongate tube to pump, wherein the drive means is disposed externally of the elongate tube.

7. A system as claimed in claim 5 wherein said pump is a diaphragm pump in which the second portion of the tube is connected via one-way inlet and outlet valves to a chamber having a diaphragm wall portion which is reciprocally displaceable by a pump motor and reciprocating drive output member inter-engaged with the outside of the diaphragm wall.

8. A system as claimed in claim 5 wherein said pump is a peristaltic pump.

9. A system as claimed in claim 3, wherein the pump means is formed and arranged so as to provide a fluid flow rate of not less than a minimum flow rate corresponding to a maximum fluid residence time within said irradiation area required for efficient mixing as indicated by the maintenance of a substantially linear relation between $\log_{10}$ kill and residence time which is obtained above said minimum flow rate and at a fluid flow rate not greater than a maximum fluid flow rate corresponding to a minimum residence time in said irradiation area required for effective inactivation of a said contaminating micro-organism by providing a desired $\log_{10}$ kill of said micro-organism, wherein said minimum residence time in said irradiation area is defined in accordance with the following relationship in which:

$$\log_{10} \text{kill} = \frac{K \times \text{Flux} \times \text{Residence time}}{OD \times \text{Tube Radius}},$$

wherein: Flux indicates the amount of UV radiation incident on the passage containing the fluid flow in the irradiation area, in mW·cm$^{-2}$; OD is the Optical Density of the fluid at the wavelength in the region where substantial virus inactivation takes place; K is an empirically derived constant; and Tube Radius is the internal radius of the vessel in the irradiation area, in centimetres, whereby in use of the system substantially the whole of the fluid may be exposed to a similar micro-organism inactivating level of UV-irradiation whilst minimising damage to the desired component(s) of the fluid.

10. A system as claimed in claim 9 wherein the pump means is formed and arranged to provide a fluid flow rate not greater than a fluid flow rate which provides a $\log_{10}$ kill of 4.

11. A system as claimed in claim 3, wherein the elongate tube is formed from discrete sections forming said first and second portions, and one or more connector sections disposed therebetween which, in use, interconnect said first and second portions to each other to allow a said fluid flow therethrough.

12. A system as claimed in claim 11 wherein one or more of said one or more connector sections are formed from a flexible material.

13. A system as claimed in claim 3, wherein the static flow mixing means comprises an elongate screw threaded member formed from alternate helical mixer elements of opposite handed screw thread.

14. A system as claimed in claim 3, wherein the first portion of the tube is formed from a material having a UV-transmissibility of at least 50% at about 254 nm.

15. A system as claimed in claim 3, wherein more than one length of said elongate tube is disposed in the irradiation zone adjacent the UV-radiation source lamp so that the first portion comprises a plurality of lengths of substantially UV transparent tubing containing static mixer elements, which lengths are inter-connected in series by connecting sections.

16. A system as claimed in claim 3, wherein said system is powered by a portable power source selected from one or more of the group consisting of at least one battery, at least one rechargeable battery, at least one solar cell, and a manually driven dynamo.

17. A system as claimed in claim 3, wherein the pump means is formed and arranged to provide at least one fluid flow rate in the range from 2 ml/min to 100 ml/min.

18. A system as claimed in claim 3, wherein said first portion is made of heat shrinkable tubing which has been shrunk to have an internal diameter equal to the diameter of said static flow mixing means.

* * * * *